United States Patent [19]

Weber et al.

[11] 4,225,515

[45] Sep. 30, 1980

[54] ISOMERIC HYDROXYMETHYL-FORMYL-TRICYCLO[5,2,1,0$^{2,6}$]DECANE MIXTURE AND PROCESS FOR MANUFACTURE THEREOF

[75] Inventors: Jürgen Weber, Oberhausen; Heinz Grau, Schwäbisch Gmünd, both of Fed. Rep. of Germany

[73] Assignee: Ruhrchemie Aktiengesellschaft, Oberhausen, Fed. Rep. of Germany

[21] Appl. No.: 954,682

[22] Filed: Oct. 25, 1978

Related U.S. Application Data

[62] Division of Ser. No. 799,114, May 20, 1977, Pat. No. 4,146,505.

[30] Foreign Application Priority Data

May 25, 1976 [DE] Fed. Rep. of Germany ....... 2623285

[51] Int. Cl.$^2$ ....................... C07C 47/34; C07C 45/08

[52] U.S. Cl. ..................................... 568/444; 568/445

[58] Field of Search ......................................... 260/598

[56] References Cited

U.S. PATENT DOCUMENTS

| | | | |
|---|---|---|---|
| 2,749,328 | 6/1956 | Cline | 260/598 X |
| 2,817,673 | 12/1957 | Roelen et al. | 260/598 X |
| 2,841,614 | 7/1958 | Buchner et al. | 260/598 X |
| 2,850,536 | 9/1958 | Buchner et al. | 260/598 X |
| 2,875,244 | 2/1959 | Bartlett et al. | 260/598 X |
| 3,499,932 | 3/1970 | Pruett et al. | 260/598 |

*Primary Examiner*—Bernard Helfin

*Attorney, Agent, or Firm*—Sprung, Felfe, Horn, Lynch & Kramer

[57] ABSTRACT

A perfume composition comprising an isomeric hydroxymethyl tricyclo(5,2,1,0$^{2,6}$)-decane of the formula

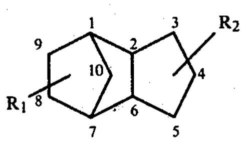

wherein $R_1$ and $R_2$ are the hydroxymethyl $CH_2OH$ or the formyl CHO group and $R_1$ represents $CH_2OH$, when $R_2$ is CHO and vice versa or a mixture thereof.

2 Claims, No Drawings

ISOMERIC HYDROXYMETHYL-FORMYL-TRICYCLO[5,2,1,$0^{2,6}$]DECANE MIXTURE AND PROCESS FOR MANUFACTURE THEREOF

This is a division of application Ser. No. 799,114 filed May 20, 1977 and now U.S. Pat. No. 4,146,505.

BACKGROUND OF THE INVENTION

Field of the Invention

This invention relates to a new isomeric hydroxymethyl-formyl-tricyclo(5,2,1,$0^{2,6}$)-decane mixture, to its production and to its use in a perfume composition (to the perfume composition and the process of the production of the perfume composition). More especially, this invention relates to a perfume composition containing at least one hydroxymethyl formyl tricyclo(5,2,1,$0^{2,6}$)-decane containing a hydroxymethyl group and a formyl group. This invention is particularly concerned with an isomeric mixture of certain hydroxymethyl-formyl tricyclo(5,2,1,$0^{2,6}$)-decanes.

The odor of musk has been highly valued for a long time. The mask pods (dried glands of the musk deer) are the most important animal source. Because this natural product is extremely expensive, repeated attempts were made in the laboratory to duplicate this odor. The fragrance of the synthetical musks varies considerably from that of the natural musk. Even very expensive synthetic products do not adequately posses the required fragrance.

It is known from German Auslegeschrift No. 23 07 627 that isomeric tricyclo(5,2,1,$0^{2,6}$)-decane-4,8(9)-dimethylols can be used as components for perfumes which have a musk-like odor. The above polycyclodimethylols have themselves a weak, pleasant odor. It is however desirable for various applications to have perfumes available which themselves have a far more distinct musk odor without loss of the pleasant fragrance.

Summary of the Invention

In accordance with the present invention there is provided the new product hydroxymethyl-formyl-tricyclo(5,2,1,$0^{2,6}$)-decane of the formula

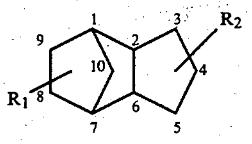

wherein $R_1$ and $R_2$ are the hydroxymethyl group $CH_2OH$ or the formyl group CHO and $R_1$ represents $CH_2OH$ when $R_2$ is CHO and vice versa.

The invention contemplates an isomeric mixture of such hydroxymethyl formulas. Such compounds or mixture of such compounds exhibits a strongly adherent animal odor, similar to Tonkin musk.

Among the isomeric hydroxymethyl-formyl-tricyclodecanes, in accordance with the above formula, are substances which contain both a hydroxymethyl and a formyl group. The hydroxymethyl group is in positions 3, 4, or 5, when the formyl group occupies positions 8 or 9 and vice versa. All conformation isomers, which correspond to the above-named formula, are included.

The isomeric hydroxyaldehydes can be prepared from partial hydrogenation of dialdehydes obtained from dicyclopentadiene by the oxo synthesis.

The hydroformylation of di-cyclo-pentadiene to diformyl-tricyclo-decane is carried out at temperatures between 100° C. and 130° C. and at synthesis gas pressures between 250 and 350 bar. The subsequent hydrogenation, which leads to the desired hydroxy aldehyde is conducted with commercially avail-able nickel catalysts at temperatures between 100° C. and 130° C. and at a hydrogen pressure of about 100 bar. By means of analytical monitoring the reaction is interrupted at the hydroxialdehyde stage.

The partial hydroformylation of dicyclopentadiene forming an unsaturated aldehyde, that can be carried out only by using very small catalyst amounts (rhodium-2-ethyl-hexanoate) and in applying temperatures below 100° C., the acetalization of this compound which takes place in simple manner by addition of e.g. methanol in acidic environment, the hydroformylation of the remaining aldehyde group and the deacetalization of the reaction product also results in the formation of an isomeric mixture of such hydroxyaldehydes.

The hydroformylation of the (still present) second double bond occurs expediently at temperatures above 100° C., preferably at 100° C. to 130° C., and at synthesis gas pressures between 250 and 300 bar increasing catalyst concentration. The hydrogenation of the aldehyde group which has been formed can take place with hydrogen using suitable hydrogenation catalysts in the known manner.

The resulting hydroxyaldehydemixture is a highly viscous substance with the typical Tonkin musk odor. If required this substance can be removed from adhering byproduct by means of a bisulfit addition product.

Like the natural animal musk the product according the invention has an exalting effect which means that the strength of odors is considerable improved. Moreover, the new product has the effect, that parfume compositions in which it is used, have a even harmonical odor, meaning that strong individual odors, which are undesired in good perfumes are avoided.

The odor of the product according the invention can be mistaken for natural animal musk odor. The new product has an odor musk closer to natural musk than the odor of even very expensive synthetic musks such as the cyclopentadecanolide.

This surprising result is ascertained by experienced perfumeurs as well as by an animal test, which is described below in the paragraph "Odour test". Example 2 confirms this unusual result: a standard example of a perfume composition of natural animal musk tincture was substituted by the corresponding tincture of the product according the invention. This verifies this unusual result. It was surprising that the product according the invention which could be manufactured readily and inexpensively has such an extraordinary good fragrance.

According to a special method of execution of the invention, hydroxymethyl-formyl-tricyclodecanes together with one of more alcohols are employed in perfume compositions. The alcohols are present as such in the hydroxyaldehyde mixture. They can, however, also react forming acetals. Suitable alcohols are mono- and polyhydric alcohols, preferably ethyl and isopropyl alcohol, glycols and glycol ether, cyclic alcohols as well as benzyl and phenylethyl alcohol. Isomeric tricyclo(5,2,1,$0^{2.6}$)-decane-3(4,5),8(9)-dimethylol is especially suitable due to its pronounced fixative properties.

Generally speaking, the isomeric hydroxymethylformyl-tricyclo(5,2,1,$0^{2.6}$)-decanes are employed in a perfume composition containing at least one of the following general types of components: alcohols with weak odor, glycols, glycol ethers, polyglycols, adipates, phthalates.

An example of the types of components present in the perfume composition to which the hydroxy aldehydes of the present invention are added include: ethyl alcohol, isopropyl alcohol, n-propenol, benzyle alcohol, phenylethylalcohol, phenoxyethyl alcohol, isotridecylalcohol 1,2-propylenglysol, dipropylenglycol, triethylenglycol diethyleneglycolmonoethylether and higher homologues, dibutyleneglycolmonoethylether, polyglycols up to a molecular weight of 600 dimethylphthalat with isomers and the homologues up to didecyclphthalate dimethyladipate with isomers and their homologues up to di-decyclophthalte, diisopropylhexanedioante.

The above mentioned alcohols with a weak odor as well as glycols, glycol ether polyglycole adipates and phthalates serve as solvents. The isomeric hydroxymethylformyl-tricyclo(5,2,1,$0^{2.6}$)-decanes, which possess a high viscosity are dissolved in the mentioned solvents in ratios of 0,1 boss 12 weight parts decane to 100 weight parts of the prepared solution. Beside their rate as solvent they also serve as important odor influencing components.

These solutions called musk bases, are intermediates which are initially manufactored preferably to perfume oils in the perfume industry. The solutions serve as constituents of all kinds of fragrant products: such as perfumes, eau de Cologne, soaps, washing agents, industrial products and cosmetics.

The mentioned alcohols serving as solvents have the further effect of stabilizing the normally reactive aldehyde group. All above mentioned alcoholic solvents increase the moschus odor property.

An unexpected increase in the odor qualities and odor strength is attained when the hydroxymethyl-formyl-tricyclo(5,2,1,$0^{2.6}$)-decanes are dissolved in isomeric tricyclo(5,2,1,$0^{2.6}$)-decane-3(4,5),8(9)-dimethylol. Beside its fixative properties, which effect a long-lasting odor by retarding the evaporation without an unfavorable influence on the odor quality the mentioned dimethylol provides for a multiple increase in odor strength compared to other musk solutions. The mentioned decane and dimethylol interact in a synergistic manner. The effect of the simultaneous application of hydroxymethyl-formyltricyclo(5,2,1,$0^{2.6}$)-decanes and (5,2,1,$0^{2.6}$)-decane-3(4,5),8(9)-dimethylols in standard perfume compositions are shown in examples 1 and 3 below. Especially favorable musk bases are obtained by mixing 0.5–20 weight percent of the mentioned decanes with the corresponding 80–99.5 weight percent di-methylol.

An hydroxy aldehyde mixture can be formed in accordance with the following examples:

PREPARATORY EXAMPLE A 1000 gram dicyclopentadiene, mixed with toluene in the weight ratio 1:1, are hydroformylated in a 5-liter high pressure steel vessel in the presence of rhodium-2-ethylhexanoate with a rhodium content of 5 milligrams at a pressure of 270 bar and a temperature of 90° C. The synthesis gas used was a volume ratio of $CO/H_2$ of 1:1. The conversion rate is monitored by continuous determination of the iodine number and the carbonyl number. When the iodine number falls below 190 the reaction is stopped by releasing and cooling the pressure vessel.

The diacetal is synthesised by addition of 500 milliliter methanol and acid treatment with paratoluene sulfonic acid to the reaction product of the first stage. After neutralisation (pH 7) the second double bond is hydroformylated in a second hydroformylation step at a temperature of 130° C. and a pressure of 270 bar with synthesis gas of a volume ratio of 1:1 in presence of 100 milligram rhodium in form of 2-ethylhexanoate. When the iodine number falls below 5, the reaction is stopped. Thereafter the whole reaction product is hydrogenated for three hours in presence of 100 gram of a nickel-hydrogenation catalyst consisiting of 55 weight percent nickel, 4.4 weight percent MgO, 33 weight percent kieselguhr and oxygen (part of the nickel is oxidized) in a steel pressure vessel at a temperature of 100° C. and at a pressure of 100 bar.

After separating the rhodium- and nickelcatalyst by filtration the deacetalization is performed in acidic medium (paratoluene sulfonic acid) by distilling the methanol. After the subsequent destillative separation of the toluene the isomeric mixture of the hydroxymethyl tricyclo(5.2.1.$0^{2.6}$)-decane of the formula is obtained as product

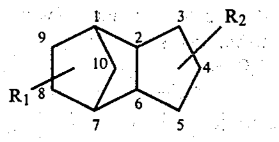

wherein $R_1$ and $R_2$ are the hydroxymethyl $CH_2OH$ or the formyl CHO group and $R_1$ represents $CH_2OH$, when $R_2$ is CHO and vice versa.

The reaction product is characterized by determinate of the hydroxy number and the carbonyl number. The product is highly viscous and has a strong musk odor.

PREPARATORY EXAMPLE B 1000 gram dicyclopentadiene mixed with toluene in the weight ratio of 1:1 are hydroformylated to diformyl-tricyclodecane in a steel high pressure vessel at a temperature of 130° C. and a pressure of 270 bar with synthesis gas with a volum ratio of $CO/H_2$ of 1:1 in presence of 100 milligram rhodium in form of 2-ethylhexanoate. When the iodine number falls below 10 (after about 4 hours) the reaction is stopped. The reaction product is hydrogenated without any further pretreatment at a temperature of 100° C. and at a pressure of 80 bar in presence of the same nickel hydrogenation catalyst that has been used in Preparatory Example A. The supply of hydrogen is adjusted in order that the reaction is carried out so far, that the reaction product includes 70 weight percent hydroxyaldehydemixture of the formula pursuant Preparatory Example A (calculated without soluent). The reaction is monitored by continuous determination of the hydroxylnumber, the CO-number and by gaschromatiphical analysis.

PREPARATORY EXAMPLE C

Purification of the hydroxyaldehyde

Aqueous sodium bisulfite solution is slowly added dropwise to the reaction product (hydroxy aldehyde)

and the mixture is stirred for 30 minutes using a turbostirrer. The bisulfite addition product is thereby deposited in crystalline form. After filtration and washing with water it is cleaved on adding formalin solution. The pure hydroxyaldehyde forms an oily phase.

The pure aldehyde exhibits a purity of 98% based on its hydroxy-carbonyl number and a gas chromatogramme.

Odour test

Odour test strips, which were moistened with different musk tinctures were put before dogs (dachshunds). The tincture was made by mixing the respective musk component (3 weight percent) with ethylalcohol. The alcohol could evaporate from the odour test strip. The first odour test strip was moistened with 3 wt.% tinctured musk pods (dried glands of the musk deer) in ethylalcohol. Immediately on smelling the odour test strip the dachshunds went to the odour test strip and bit into it. The second odour test strip was treated in the same manner with a tincture of 3 weight percent 6-acetyl-1,1,3,4,4,6-hexamethyltetrahydronaphthalene (Tonalid, a synthetical polycyclic musk) in ethylalcohol. The third odour test strip was treated in the same manner with a tincture of 3 weight percent 1,3,4,6,7,8-hexahydro-4,6,6,7,8,8-hexamethylcyclopenta-γ-2-benzopyrene (Galaxolid, also a synthetic polycyclic musk) in ethylalcohol.

The dachshunds didn't take any notice of the second and third odour test strips when they were put before them.

The forth odour test strip was moistened with an ethylalcohol tincture of 3 weight percent of the isomeric hydroxymethyl tricyclo $(5,2,1,0^{2.6})$-decane mixture of the formula

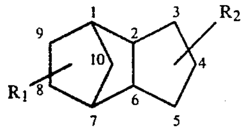

wherein $R_1$ and $R_2$ are the hydroxymethyl $CH_2OH$ or the formyl CHO group and $R_1$ represents $CH_2OH$, when $R_2$ is CHO and vice versa according to our invention.

The dachshunds behaved in the same manner as did with the first odour test strip: they went to the odour test strip immediately when put before it and bit into the strip.

The fifth odour test strip was moistened with an ethylalcohol tincture of 3 weight percent of cyclopentadecanolide. When put before the dogs, they didn't take any notice of the fifth odour test strip.

In order to more fully illustrate the nature of the invention and the manner of practicing the same, the following examples are presented:

EXAMPLE 1

Perfume composition with the following components:

| | |
|---|---|
| 100 g | ladanum absolue |
| 50 g | vetiverol |
| 10 g | patchouli oil |
| 50 g | bergamot oil |

-continued

| | |
|---|---|
| 30 g | rose absolue |
| 50 g | ambrette musk |
| 50 g | ketone musk |
| 40 g | vanillin |
| 100 g | gamma methyl ionone |
| 40 g | scarlet sage oil |
| 80 g | East Indian sandalwood oil |
| 20 g | cypress oil |
| 20 g | tube rose absolue |
| 30 g | decolored oak moss |
| 150 g | ambergris tincture (3% in ethanol) |
| 30 g | iris concret |
| 50 g | sweet orange oil |
| 23 g | tricyclo$(5,2,1,0^{2,6})$-decane-3(4,5),8(9)-dimethyl (isomeric mixture) |
| 2 g | hydroxymethyl-formyl-tricyclo$(5,2,1,0^{2,6})$-decane (isomeric mixture) |
| 75 g | ethanol |
| 1000 g | |

The composition has a distinctive amber odor and has a more lasting effect on the skin than the same composition without the addition of the isomeric hydroxymethylformyl-tricyclo-$(5,2,1,0^{2,6})$-decane mixture.

EXAMPLE 2

Perfume composition with the following components:

| | |
|---|---|
| 60 g | birch tar oil rect. |
| 440 g | castoreum tincture (5% in ethanol) |
| 30 g | rose oil |
| 110 g | bergamot oil |
| 5 g | East Indian sandalwood oil |
| 1 g | patchouli oil |
| 8 g | jasmine absolute |
| 15 g | ambrette musk |
| 15 g | ketone musk |
| 15 g | Fleur d'Oranger absolue |
| 15 g | neroli oil |
| 3 g | coumarin |
| 8 g | vanilla tincture (3% in ethanol) |
| 18 g | artificial amber |
| 2 g | vanillin |
| 10 g | zibeth absolue (10% in ethanol) |
| 8 g | cassia absolue |
| 1 g | iris concret |
| 10 g | Messina lemon oil |
| 6 g | mace oil |
| 30 g | opoponax resinoid |
| 2 g | hydroxymethyl-formyl-tricyclo$(5,2,1,0^{2,6})$-decane (isomeric mixture) |
| 188 g | ethanol |
| 1000 g | |

The composition has the typical fragrance of a "Russian-leather" perfume with a longer lasting effect and a stronger diffusion than the same mixture in which the hydroxymethyl-formyl-tricyclo$(5,2,1,0^{2.6})$-decane-isomeric mixture and 188 g ethanol are substituted by 190 g of a 3 percent musk tincture.

EXAMPLE 3

Perfume composition with the following components:

| | |
|---|---|
| 27 g | ylang-ylang extra |
| 65 g | linalool |
| 55 g | synthetic tube-rose absolute |
| 35 g | synthetic neroli oil |
| 70 g | Fleur d'Oranger absolue |
| 55 g | vanillin |
| 70 g | jasmine absolue |

-continued

| | |
|---|---|
| 55 g | Turkish rose oil |
| 15 g | phenylethyl alcohol |
| 3 g | iris concret |
| 300 g | Messina lemon oil |
| 25 g | geranium oil |
| 80 g | zibeth absolue (10% in ethanol) |
| 70 g | benzoic Siam resinoid |
| 7.3 g | tricyclo(5,2,1,$0^{2,6}$)-decane-3-(4,5),8(9)-dimethylol (isomeric mixture) |
| 0.2 g | hydroxymethyl-formyl-tricyclo(5,2,1,$0^{2,6}$)-decane |
| 67.5 g | ethanol |
| 1000 g | |

The composition yields a perfume oil with a similar fragrance to "Magnolia". The former has a longer lasting odor diffusion and a livlier effect than the same composition without the addition, according to the invention, of the isomeric hydroxymethyl-formyl-tricyclo(5,2,1,$0^{2.6}$)-decane mixture.

What is claimed is:

1. An isomeric hydroxymethylformyltricyclo(5,2,1,$0^{2.6}$)-decane mixture of the formula

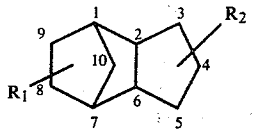

wherein $R_1$ and $R_2$ are the hydroxymethyl $CH_2OH$ of the formyl CHO group and $R_1$ represents $CH_2OH$, when $R_2$ is CHO and vice versa wherein each component of the isomeric mixture contains both a hydroxymethyl and a formyl group and the hydroxymethyl group is in the 3, 4 or 5 position when the formyl group occupies position 8 or 9 and the formyl group is in the 3, 4 or 5 position when the hydroxymethyl group is in position 8 or 9.

2. Process for the manufacture of the product according to claim 1 comprising the hydroformylation of dicyclopentadiene to diformyltricyclodecane at temperatures of 100° to 130° C., pressures of 250 to 350 bar and in presence of cobalt or rhodiumcatalysts and partial hydrogenation of the dialdehyde at temperatures of 100° to 130° C. and a hydrogen pressure of 100 bar.

* * * * *

UNITED STATES PATENT AND TRADEMARK OFFICE

CERTIFICATE OF CORRECTION

PATENT NO. : 4,225,515

DATED : September 30, 1980

INVENTOR(S) : Jurgen Weber and Heinz Grau

It is certified that error appears in the above—identified patent and that said Letters Patent is hereby corrected as shown below:

| Column | Line | |
|---|---|---|
| 1 | 25 | "mask" should be --musk--. |
| 3 | 14 | "propylenglysol" should be --propylenglycol-- |
| 3 | 21 | "hexanedioante" should be --hexanedionate--. |

Signed and Sealed this

*Thirteenth* Day of *January 1981*

[SEAL]

*Attest:*

SIDNEY A. DIAMOND

*Attesting Officer* *Commissioner of Patents and Trademarks*